United States Patent
Farmer et al.

(10) Patent No.: US 12,000,016 B2
(45) Date of Patent: Jun. 4, 2024

(54) ENVIRONMENTALLY-FRIENDLY COMPOSITIONS AND METHODS FOR EXTRACTING MINERALS AND METALS FROM ORE

(71) Applicant: Locus Solutions IPCo, LLC, Solon, OH (US)

(72) Inventors: Sean Farmer, North Miami Beach, FL (US); Ken Alibek, Solon, OH (US); Samal Ibragimova, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 812 days.

(21) Appl. No.: 16/955,927

(22) PCT Filed: Dec. 22, 2018

(86) PCT No.: PCT/US2018/067408
§ 371 (c)(1),
(2) Date: Jun. 19, 2020

(87) PCT Pub. No.: WO2019/133554
PCT Pub. Date: Jul. 4, 2019

(65) Prior Publication Data
US 2020/0340076 A1    Oct. 29, 2020

Related U.S. Application Data
(60) Provisional application No. 62/610,581, filed on Dec. 27, 2017.

(51) Int. Cl.
| | | |
|---|---|---|
| C22B 3/18 | (2006.01) | |
| C12N 1/16 | (2006.01) | |
| C12N 1/20 | (2006.01) | |
| C22B 3/00 | (2006.01) | |
| C22B 3/02 | (2006.01) | |
| C22B 11/00 | (2006.01) | |
| C22B 15/00 | (2006.01) | |
| C22B 19/20 | (2006.01) | |
| C22B 26/12 | (2006.01) | |

(52) U.S. Cl.
CPC ............... *C22B 3/18* (2013.01); *C12N 1/16* (2013.01); *C12N 1/20* (2013.01); *C22B 3/02* (2013.01); *C22B 11/042* (2013.01); *C22B 15/0065* (2013.01); *C22B 19/20* (2013.01); *C22B 23/0407* (2013.01); *C22B 26/12* (2013.01)

(58) Field of Classification Search
CPC .......... C22B 3/18; C22B 3/02; C22B 11/042; C22B 15/0065; C22B 19/20; C22B 23/0407; C22B 26/12; C12N 1/15; C12N 1/20
USPC ........................................................ 423/27
See application file for complete search history.

(56) References Cited

U.S. PATENT DOCUMENTS

| | | |
|---|---|---|
| 5,021,088 A | 6/1991 | Portier |
| 5,800,593 A | 9/1998 | Kohr |
| 2002/0037245 A1 | 3/2002 | Galina |
| 2010/0055199 A1 | 3/2010 | Mansoori |
| 2015/0037302 A1 | 2/2015 | Bralkowski et al. |
| 2015/0275328 A1 | 10/2015 | Walder et al. |
| 2022/0055042 A1 | 2/2022 | Farmer et al. |

FOREIGN PATENT DOCUMENTS

| | | |
|---|---|---|
| CN | 104140822 A | 11/2014 |
| CN | 105567580 A | 5/2016 |
| CN | 107365585 A | 11/2017 |
| KR | 20120016995 A | 2/2012 |
| WO | 2017044953 A1 | 3/2017 |

OTHER PUBLICATIONS

Camargo, F.P., et al., "Characterization of Biosurfactant from Yeast Using Residual Soybean Oil Under Acidic Conditions and Their Use in Metal Removal Processes." FEMS Microbiology Letters, 2018, 365(10): 1-8.

Castaneda, L.C., et al., "Current Situation of Emerging Technologies for Upgrading of Heavy Oils." Catalysis Today, 2014, 220-222: 248-273.

De Almeida, D.G., et al., "Biosurfactants: Promising Molecules for Petroleum Biotechnology Advances." Frontiers in Microbiology, 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Kurtzman, C.P., et al., "Production of sophorolipid biosurfactants by multiple species of the Starmerella (*Candida*) pombicolayeast clade." FEMS Microbiol Lett, 2010, 311: 140-146.

Pacwa-Plociniczak, M., et al., "Environmental Applications of Biosurfactants: Recent Advances." International Journal of Molecular Sciences, 2011, 12: 633-654.

Sen, R., "Biosurfactants: Advances in Experimental Medicine and Biology." Landes Bioscience and Springer Science+Business Media, LLC, 2010, 672: 1-331.

Sharma, A., et al., "A Study on Biosurfactant Production in *Lactobacillus* and *Bacillus* SP." International Journal of Current Microbiology and Applied Sciences, 2014, 3(11): 723-733.

(Continued)

*Primary Examiner* — Melissa S Swain
(74) *Attorney, Agent, or Firm* — SALIWANCHIK, LLOYD & EISENSCHENK

(57) ABSTRACT

The subject invention provides safe, environmentally-friendly, compositions and methods for extracting minerals and/or metals from ore. More specifically, the subject invention provides for bioleaching using a composition comprising one or more biosurfactant-producing microorganisms and/or microbial growth by-products. In specific embodiments, the composition comprises biosurfactant-producing yeasts and/or their growth by-products.

8 Claims, No Drawings

(56) References Cited

OTHER PUBLICATIONS

Brady, D., et al., "Chemical and Enzymatic Extraction of Heavy Metal Binding Polymers from Isolated Cell Walls of *Saccharomyces cerevisiae*." Biotechnology and Bioengineering, 1994, 44: 297-302.

Brandl, H., "Microbial Leaching of Metals." Biotechnology, 2001, 10: 191-224.

Diaz, M.A., et al., "Metal Removal from Contaminated Soils Through Bioleaching with Oxidizing Bacteria and Rhamnolipid Biosurfactants." Soil and Sediment Contamination, 2015, 24: 16-29.

Karwowska, E., et al., "Bioleaching of metals from printed circuit boards supported withsurfactant-producing bacteria." Journal of Hazardous Materials, 2014, 264: 203-210.

Krebs, W., et al., "Microbial recovery of metals from solids." FEMS Microbiology Reviews, 1997, 20: 605-617.

Lee, J., et al., "Bio-processing of solid wastes and secondary resources for metal extraction—A review." Waste Management, 2012, 32: 3-18.

Liang, X., et al., "Fungal formation of selenium and tellurium nanoparticles." Applied Microbiology and Biotechnology, 2019, 103: 7241-7259.

Liang, X., et al., "Metal and metalloid biorecovery using fungi." Microbial Biotechnology, 2017, 10(5): 1199-1205.

Mulligan, C.N., et al., "Bioleaching of copper and other metals from low-grade oxidized mining ores by Aspergillus niger." Journal of Chemical Technology and Biotechnology, 2003, 78: 497-503.

Mulligan, C.N., et al., "Bioleaching of heavy metals from a low-grade mining ore using Aspergillus niger." Journal of Hazardous Materials, 2004, 110: 77-84.

Seidel, H., et al., "Bioleaching of heavy metal-contaminated sediments by indigenous *Thiobacillus* spp: metal solubilization and sulfur oxidation in the presence of surfactants." Appl. Microbiol. Biotechnolo., 2000, 54: 854-857.

Vahabi, K., et al., "Biosynthesis of Silver Nano-Particles by Trichoderma and Its Medical Applications." Biotechnology and biology of Trichoderma, 2014, Elseview, pp. 393-404.

Valix, M., et al., "Fungal Bio-Leaching of Low Grade Laterite Ores." Minerals Engineering, 2001, 14(2): 197-203.

Wu, H-Y., et al., "Metal extraction from municipal solid waste (MSW) incinerator fly ash—Chemical leaching and fungal bioleaching." Enzyme and Microbial Technology, 2006, 38: 839-847.

Yang, Z., et al., "Bioleaching remediation of heavy metal-contaminated soils using *Burkholderia* sp. Z-90." Journal of Hazardous Materials, 2016, 301: 145-152.

ENVIRONMENTALLY-FRIENDLY COMPOSITIONS AND METHODS FOR EXTRACTING MINERALS AND METALS FROM ORE

CROSS-REFERENCE TO RELATED APPLICATION

This application is a National Stage Application of International Application No. PCT/US2018/067408, filed Dec. 22, 2018; which claims priority to U.S. Provisional Application No. 62/610,581, filed Dec. 27, 2017, both of which are incorporated herein by reference in its entirety.

BACKGROUND OF THE INVENTION

"Leaching" is a widely used extractive metallurgy technique that converts metals found in ore (pieces of mineral, rock or soil) into soluble salts in aqueous media. There are a variety of leaching processes, usually classified by the types of reagents used. These techniques utilize either chemicals or microorganisms to extract metals, depending upon the ores or materials to be processed.

One leaching technique, called heap leach mining provides a low-cost method of extracting metal values from relatively low-grade metal-bearing materials, and has found particular application in the processing of metal-bearing ores. Heap leach mining uses a series of chemical reactions that absorb specific minerals and then re-separates them after their division from other earth materials in the ore. Generally, an ore is mined, crushed, and then transported to a heap location where it is stacked onto an impervious liner, or heap leach pad.

The ore is continuously sprayed or irrigated with a suitable solution, or process fluid. Process fluids can be alkaline or acidic. For example, a dilute alkaline cyanide solution, ozone and sulfuric acid can be used, depending on the substrate being extracted.

The process fluid extracts metals in the ore upon contact with the ore and the resulting "pregnant solution" trickles slowly under the force of gravity to the pad. The heap leach pad typically has a sloped base to allow pregnant solution to flow into collection drains for separating the metal from the process fluid. The percolation of solution through the heap is called the "leach cycle," which can take from one or two months for simple oxide ores (e.g., most gold ores) up to two years (for nickel laterite ores).

After separating the precious metals from the pregnant solution, the dilute cyanide solution (now called "barren solution") is normally re-used in the heap-leach-process or sent to an industrial water treatment facility, where the residual cyanide or acid is treated and residual metals are removed.

Although heap leaching can be a low-cost process, normal recovery rates range from 60-70%, although there are exceptions. It is normally most profitable with low-grade ores. Higher-grade ores are usually put through more complex milling processes, where higher recoveries justify the extra cost. The process chosen depends on the properties of the ore.

Additionally, for the leaching of certain precious metals, such as gold and silver, leaching reagents include cyanide, thiosulfate, thiocyanate, halides and halogens (e.g., chlorides, bromides, iodides, chlorine, bromine and iodide), and thiourea. Of these, cyanide remains the predominant reagent applied on industrial scales for gold and gold-silver ores. Halides (chlorine and chlorides in particular) are often used in the final refining of impure bullion (bars, coins or ingots of a metal). Furthermore, metallic mercury, which is highly poisonous and environmentally hazardous, is still used by many artisanal miners.

Despite being a robust leaching reagent (or lixiviant), use of sodium cyanide, and cyanides of other alkali metals (e.g., potassium) and alkali earth metals (e.g., calcium), poses a number of challenges, principally due to its toxicity, regulatory restrictions, high carbon footprint and low selectivity in low grade ores. It is particularly problematic for gold ores with high copper and/or high silver content, as copper is often present at levels of around 1000 times the gold concentration, leading to excessive cyanide consumption, and removal of available cyanide for gold leaching. Cyanide is also an expensive reagent, so that using it for lower value metals such as copper (and less so, for silver) quickly becomes uneconomic, not only for leaching, but also due to downstream impacts. In addition, it generates weak acid dissociable (WAD) cyanides, which further require cyanide detoxification/destruction or recovery processes.

Heap leaching can be used for extracting, for example, nickel, copper and gold. Leaching of certain other compounds often involves the use of pressurized vessels, called autoclaves. Cobalt, for example, is commonly produced using high pressure acid leaching (HPAL). The process utilizes temperatures around 255° C. and pressures around 725 psi, in addition to sulfuric acid to separate the metal from the ore.

In HPAL, the ore is mined and crushed to create a fine material, which is mixed with water to create a slurry. The slurry is heated and pumped into an autoclave, to which acid is added. The slurry and acid then react as they flow through several compartments within the autoclave. It takes approximately 60 minutes to complete the leaching process in the autoclave. Upon leaving the high pressure and temperature atmosphere of the autoclave, the slurry must be returned to atmospheric conditions. This is accomplished through two or more letdown/flash stages. Once the slurry is at atmospheric conditions it is washed and separated, at which point the metal can be recovered from the liquid fraction.

Leaching processes may be enhanced by the use of microorganisms, such as thermophilic and/or acidophilic bacteria that grow on the surface and in the cracks of ore fragments. This process of "bio-stimulation" can provide, for example, catalyzation of oxidation reactions within the ore. Such a process typically involves use of a high concentration of microbes.

Microorganisms themselves can also be used to carry out leaching, through "bioleaching." Typically, bioleaching requires a slurry containing carbon dioxide and other microbial nutrients, sulfide concentrate and microbes, as well as tanks, microbial monitoring systems, and control of pH and redox potential.

Biological leaching processes are more environmentally-friendly alternatives to conventional smelting processes, which discharge large amounts of carbon dioxide, sulfur dioxide, and various toxic materials, such as arsenic, into the environment. Currently known bio-stimulation and bioleaching processes have a number of disadvantages, however. They can be time consuming and cost-inefficient. For example, bioleaching of copper concentrates is typically very slow, with incomplete recoveries achieved even after many weeks to months of leaching.

Additionally, it can be costly and cumbersome to transport and keep microbes viable at a site of application. Currently, microbe-based leaching operations are limited to sourcing microbial amendments from far-flung producers whose product quality suffers due to upstream processing delays, methods used to stabilize the product for future distribution, supply chain bottlenecks, improper storage, and other factors that inhibit the timely delivery and application of viable, high cell-count microbial products.

Accordingly, there is a need for improved compositions and methods for extracting valuable minerals and/or metals from ore.

BRIEF SUMMARY OF THE INVENTION

The subject invention relates generally to metals recovery. More specifically, the subject invention relates to microbes, as well as by-products of their growth, such as biosurfactants, solvents, and/or enzymes, for use in bioleaching.

In specific embodiments, the subject invention provides microbe-based compositions and methods for recovering valuable minerals and/or metals, such as, e.g., gold, copper, silver, lithium and cobalt, from ore and/or mine tailings. These compositions, and the methods of their use, are safe, environmentally-friendly and cost-efficient.

In preferred embodiments, the microbe-based composition of the subject invention is an environmentally-friendly biological leaching reagent comprising one or more microorganisms and/or microbial growth by-products. In one embodiment, at least one of the microorganisms is a biosurfactant-producing yeast.

In one embodiment, the microbial growth by-products are biosurfactants, enzymes, proteins, peptides, amino acids and/or solvents. In one embodiment, the microbial growth by-products are biosurfactants. Biosurfactants according to the subject invention include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

In some embodiments, the growth by-product is produced by the one or more microorganisms present in the composition. In some embodiments, the growth by-product is added to the composition, either in crude or purified form, in addition to any growth by-products that are produced by the microorganisms.

In certain specific embodiments, the biological leaching reagent comprises a yeast fermentation product comprising yeast cell biomass and growth by-products thereof in fermentation medium in which the yeast was produced. Preferably, the yeast is a biosurfactant-producing yeast. Even more preferably, the yeast is *Starmerella bombicola*, which is capable of producing glycolipid biosurfactants, e.g., sophorolipids (SLP), at high concentrations.

In some embodiments, the yeast fermentation product is obtained during production of biosurfactants. During submerged cultivation of a biosurfactant-producing microorganism, biosurfactants are excreted into the fermentation broth. The biological leaching reagent can comprise the entire broth containing microbes, biosurfactants and other growth by-products, such as, e.g., excreted metabolites and/or cell wall components.

Alternatively, the biosurfactants can be harvested from the broth for further processing and/or purification. What remains after harvesting the biosurfactants is a supernatant comprising yeast cell biomass, residual biosurfactants and other growth by-products, such as, e.g., excreted metabolites and/or cell wall components. In certain embodiments, the biological leaching reagent of the subject invention comprises this supernatant.

In certain embodiments, use of yeast fermentation products in the biological leaching reagents can be superior to, for example, purified microbial metabolites alone, due to, for example, the advantageous properties of yeast cells. These properties include, for example, high concentrations of mannoprotein and/or beta-glucan in and/or on the yeast cell wall. These compounds can serve as, for example, effective emulsifiers. Additionally, the yeast fermentation product can further comprise biosurfactants, other metabolites, and/or cellular or extracellular components that are present in the culture, such as, e.g., solvents, acids, vitamins, minerals, enzymes, proteins, peptides, amino acids and others (e.g., lactic acid, ethanol, etc.), in the culture.

In one embodiment, the biological leaching reagent can be enhanced with additional components as are needed, depending upon, for example, the ore type, mineral type, volume of ore, and other factors. These enhancing components can include additional microbial cultures, such as yeast and/or bacterial cultures. The enhancing components can also include additional pure or crude form biosurfactants, acids, solvents, enzymes, proteins, peptides, amino acids and/or other metabolites.

In some embodiments, the additional microbial cultures comprise biosurfactant-producers, such as, for example, *Wickerhamomyces anomalus, Pseudozyma aphidis, Saccharomyces cerevisiae, Pichia guilliermondii, Bacillus subtilis, Bacillus amyloliquefaciens, Bacillus licheniformis, Pseudomonas aeruginosa, Streptococcus* spp., and many others.

In some embodiments, the additional microbial cultures comprise microorganisms capable of accumulating nanoparticles of minerals and/or metals such as, for example, copper, cobalt, lithium, gold and/or silver, by solubilizing the metal present in ore to a soluble ionic form and converting it into nanoparticles within their cells. For example, thermophilic and/or acidophilic bacteria such as *Cupriavidus metallidurans*, which can precipitate nanoparticles of gold, can be added to the biological leaching reagent as an enhancement.

In some embodiments, the enhancing components comprise additional biosurfactants. The biosurfactants can be added as part of a microbial culture, or as a crude or purified form after being extracted from a microbial culture.

The biosurfactants can comprise glycolipids such as, for example, rhamnolipids (RLP), sophorolipids (SLP), trehalose lipids or mannosylerythritol lipids (MEL). In one embodiment, the biosurfactants are lipopeptides, such as, e.g., surfactin, iturin, fengycin, viscosin and/or lichenysin. In one embodiment, the biosurfactants are polymeric biosurfactants, such as, for example, emulsan, lipomanan, alasan, and/or liposan. In one embodiment, the biological leaching reagent comprises, and/or is enhanced by the addition of, more than one biosurfactant and/or biosurfactant derivative.

In certain embodiments, the subject invention provides a method for extracting valuable minerals and/or metals from ore, wherein the method comprises obtaining ore from, e.g., an ore deposit, said ore comprising one or more valuable minerals and/or metals, in addition to gangue; applying a biological leaching reagent comprising one or more microorganisms and/or microbial growth by-products, to the ore; allowing the valuable minerals and/or metals to separate from the ore; and collecting the valuable minerals and/or metals. In some embodiments, the method is performed in a tank, vat, column (e.g., unsaturated or saturated leaching column) or pool.

In one embodiment, the ore is mined and crushed, micronized, pulverized or ground into smaller particles. In one embodiment, the ore is in the form of mine tailings, or the waste products left behind after a mineral has been separated from gangue.

In a specific embodiment, the method comprises applying the biological leaching reagent in liquid form to the smaller ore particles, and mixing the particles and biological leaching reagent to form a liquid slurry.

The slurry can then be left for any amount of time sufficient to leach the valuable mineral and/or metal particles from the ore. The slurry can optionally be mixed and/or circulated continuously (e.g., mechanically or using aeration) throughout the leaching time period to ensure that maximum contact is made between the ore particles and the leaching reagent.

In one embodiment, the mineral particles are sequestered by the cells of the microorganism(s) of the biological leaching reagent. In one embodiment, the mineral particles separate from the ore and are dispersed and/or float in the liquid as solution. The liquid fraction of the slurry can be siphoned, drained, filtered, or otherwise removed. The mineral particles present in the liquid can be washed to remove residual microbial cell matter, collected, and dried, incinerated, and/or processed by any other means known in the metallurgical arts.

In some embodiments, the method comprises applying the biological leaching reagent in liquid form to a pile or column filled with the crushed ore particles, and allowing the biological leaching reagent to percolate through the particles to a collection apparatus using gravity. In some embodiments, the method can be used for bio-stimulation of heap leaching processes.

The biological leaching reagent can enhance recovery of valuable minerals and/or metals from ore due to, for example, microbial sequestration activity and/or metabolites that solubilize the minerals and/or metals from the ore.

The microbes can be live (or viable), or inactive at the time of application. In certain embodiments, the microorganisms can grow in situ and produce active compounds (e.g., metabolites) onsite. Consequently, a high concentration of desirable metabolites (e.g., biosurfactants, solvents, enzymes, proteins, peptides and amino acids) and the microorganisms that produce them can be achieved easily and continuously at a treatment site (e.g., an ore mining site or a heap leaching pile).

The method can further comprise adding materials to enhance microbe growth during application (e.g., adding nutrients).

The method can further comprise adding additional materials to enhance extraction of the valuable minerals and/or metals, for example, additional microbial cultures, such as yeast and/or bacterial cultures and/or additional pure or crude form biosurfactants, acids, solvents, enzymes, proteins, peptides and/or amino acids.

Advantageously, in certain embodiments, the methods take as little as a few hours, e.g., 3 to 12 hours, to one day to leach the minerals from the ore. The amount of time, however, depends upon, for example, how finely ground the ore particles are, the volume of ore particles being processed, and what types and/or combinations of microorganisms and other components are used in the biological leaching reagent.

Additionally, in one embodiment, the subject methods reduce the amount of refining and processing needed to recover pure or nearly pure metals from ore. For example, the subject invention can be used to separate the metals in a doré bar and reduce the amount of refining needed to do so.

The method can be carried out at atmospheric pressure and lower temperatures than traditional metal smelting operations. Thus, the method does not require complicated equipment or high energy consumption, and cultivation of the biological leaching reagent used in the subject method can be performed on site, for example, at a mine or at a leaching site.

Advantageously, the present invention can be used without releasing large quantities of inorganic and toxic compounds into the environment. Additionally, the compositions and methods utilize components that are biodegradable and toxicologically safe, and can be used to reduce the amount of toxic waste produced during mining and leaching processes.

DETAILED DESCRIPTION

The subject invention relates generally to metals recovery. More specifically, the subject invention relates to microbes, as well as by-products of their growth, such as biosurfactants, solvents, and/or enzymes, for use in bioleaching.

In specific embodiments, the subject invention provides microbe-based compositions and methods for recovering valuable minerals and/or metals, such as, e.g., gold, copper, silver, lithium and cobalt, from ore and/or mine tailings. These compositions, and the methods of their use are safe, environmentally-friendly and cost-efficient.

In preferred embodiments, the microbe-based composition of the subject invention is an environmentally-friendly biological leaching reagent comprising one or more microorganisms and/or microbial growth by-products. In one embodiment, at least one of the microorganisms is a biosurfactant-producing yeast.

In certain embodiments, the subject invention provides a method for extracting valuable minerals and/or metals from ore, wherein the method comprises obtaining ore from, e.g., an ore deposit, said ore comprising one or more valuable minerals and/or metals, in addition to gangue; applying a biological leaching reagent comprising one or more microorganisms and/or microbial growth by-products, to the ore; allowing the valuable minerals and/or metals to separate from the ore; and collecting the valuable minerals and/or metals.

The biological leaching reagent can enhance recovery of valuable minerals and/or metals from ore due to, for example, microbial sequestration activity and/or metabolites that sequester nanoparticles of the minerals and/or metals.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In some embodiments, the microbes are present, with broth in which they were grown, in the microbe-based composition. The cells may be present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$ or more propagules per milliliter of the composition. As used herein, a propagule is any portion of a microorganism from which a new and/or mature organism can develop, including but not limited to, cells, spores, conidia, hyphae, mycelia, cysts, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of a microbe-based composition from a growth vessel.

As used herein, a "biofilm" is a complex aggregate of microorganisms, such as bacteria, wherein the cells adhere to each other on a surface. The cells in biofilms are physiologically distinct from planktonic cells of the same organism, which are single cells that can float or swim in liquid medium.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, biopolymers, enzymes, toxins, acids, solvents, alcohols, proteins, peptides, amino acids, vitamins, minerals, microelements, and biosurfactants.

By "reduces" is meant a negative alteration, and by "increases" is meant a positive alteration, wherein the alteration is at least 0.001%, 0.01%, 0.1%, 1%, 5%, 10%, 15%, 20%, 25%, 30%, 35%, 45%, 50%, 55%, 60%, 65%, 70%, 75%, 80%, 85%, 90%, 95%, 99%, or 100%, inclusive of all values therebetween.

By "reference" is meant a standard or control condition.

By "salt-tolerant" is meant a microbial strain capable of growing in a sodium chloride concentration of fifteen (15) percent or greater. In a specific embodiment, "salt-tolerant" refers to the ability to grow in 150 g/L or more of NaCl.

By "surfactant" is meant a compound that lowers the surface tension (or interfacial tension) between two liquids or between a liquid and a solid. Surfactants act as, e.g., detergents, wetting agents, emulsifiers, foaming agents, and dispersants. A biosurfactant is a surfactant produced by a living cell, e.g., a microbe.

As used herein, "applying" a composition or product refers to contacting it with a target or site such that the composition or product can have an effect on that target or site. The effect can be due to, for example, microbial growth and/or the action of a biosurfactant or other growth by-product. For example, the microbe-based compositions or products can be contacted with ore by pouring and/or spraying onto the ore.

As used herein, the terms "valuable minerals" and "valuable metals" refer to any mineral or metal that is extracted or mined from the earth, which has some economic value. The value of the mineral and/or metal is typically measured by how abundant or rare it is, with rarer minerals and/or metals having a higher economic value per unit of weight over those that are more abundant.

"Precious" or "rare" metals refer to naturally occurring metallic chemical elements having the highest economic value per unit of weight due to their extreme rarity. Precious metals include rhodium, platinum, gold, palladium, indium, iridium osmium, rhenium, ruthenium and silver, (Biltmore Loan and Jewelry 2016).

As used herein, "ore" refers to a naturally occurring solid material from which a valuable mineral and/or metal can be profitably extracted. Ores are often mined from ore deposits, which comprise ore minerals containing the valuable substance. "Gangue" minerals are minerals that occur in the deposit but do not contain the valuable substance. Examples of ore deposits include hydrothermal deposits, magmatic deposits, laterite deposits, volcanogenic deposits, metamorphically reworked deposits, carbonatite-alkaline igneous related deposits, placer ore deposits, residual ore deposits, sedimentary deposits, sedimentary hydrothermal deposits and astrobleme-related deposits. Ores, as defined herein, however, can also include ore concentrates or tailings, coal or coal waste products, or even other sources of metal or valuable minerals, including but not limited to, jewelry, electronic scraps, batteries and other scrap materials.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive.

Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Biological Leaching Reagent

In specific embodiments, the subject invention provides microbe-based compositions and methods for recovering valuable minerals and/or metals, such as, e.g., gold, copper, silver, lithium and cobalt, from ore and/or mine tailings. These compositions, and the methods of their use are safe, environmentally-friendly and cost-efficient.

In preferred embodiments, the microbe-based composition of the subject invention is a biological leaching reagent comprising one or more microorganisms and/or microbial growth by-products. In one embodiment, at least one of the microorganisms is a biosurfactant-producing yeast.

The microorganisms in the microbe-based product may be in an active or inactive form, in spore form, mycelial form, or any other form of microbial propagule. Typically, the microorganism is inactive at the time it is applied to a site.

In one embodiment, the microbial growth by-product is a biosurfactant, enzyme, protein, peptide, amino acid and/or solvent. In one embodiment, the microbial growth by-products are biosurfactants. Biosurfactants according to the subject invention include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

In some embodiments, the growth by-product is produced by the one or more microorganisms present in the composition. In some embodiments, the growth by-product is added to the composition, either in crude or purified form, in addition to any growth by-products that are produced by the microorganisms.

In certain specific embodiments, the biological leaching reagent comprises a yeast fermentation product comprising yeast cell biomass and growth by-products thereof in fermentation medium in which the yeast was produced. Preferably, the yeast is a biosurfactant-producing yeast. Even more preferably, the yeast is *Starmerella bombicola*, which is capable of producing glycolipid biosurfactants, e.g., sophorolipids (SLP), at high concentrations.

In some embodiments, the yeast fermentation product is obtained during production of biosurfactants. During submerged cultivation of a biosurfactant-producing microorganism, biosurfactants are excreted into the fermentation broth. The biological leaching reagent can comprise the entire broth containing microbes, biosurfactants and other growth by-products, such as, e.g., excreted metabolites and/or cell wall components.

Alternatively, the biosurfactants can be harvested from the broth for further processing and/or purification. In one embodiment, *S. bombicola* produces a layer of SLP sediment in the culture comprising about 10-15% SLP, or about 4-5 g/L. In a specific embodiment, cultivation of the yeast occurs at 25-28° C. for 1 to 10 days. Advantageously, once the SLP layer is harvested from the culture, about 1-4 g/L of SLP can still remain in the supernatant, as well as yeast cell biomass and other advantageous yeast growth by-products and cellular components. In certain embodiments, the biological leaching reagent of the subject invention comprises the supernatant.

In certain embodiments, use of yeast fermentation products in the biological leaching reagents can be superior to, for example, purified microbial metabolites alone, due to, for example, the advantageous properties of yeast cell and/or cell walls. These properties include, for example, high concentrations of mannoprotein and/or beta-glucan in and/or on the yeast cell wall. These compounds can serve as, for example, effective emulsifiers. Additionally, the yeast fermentation product can further comprise biosurfactants, other metabolites, and/or cellular or extracellular components that are present in the culture, such as, e.g., solvents, acids, vitamins, minerals, enzymes, proteins, peptides, amino acids and others (e.g., lactic acid, ethanol, etc.), in the culture.

In one embodiment, the biological leaching reagent can further comprise nutrient sources, including sources of nitrogen, nitrate, phosphorus, magnesium and/or carbon.

In one embodiment, the biological leaching reagent can be enhanced with additional components as are needed, depending upon, for example, the ore type, mineral type, volume of ore, and other factors. These enhancing components can include additional microbial cultures, such as yeast and/or bacterial cultures. The enhancing components can also include additional pure or crude form biosurfactants, acids, solvents, enzymes, proteins, peptides and/or amino acids.

In some embodiments, the additional microbial cultures comprise biosurfactant-producers, such as, for example, *Wickerhamomyces anomalus, Pseudozyma aphidis, Saccharomyces cerevisiae, Pichia guilliermondii, Bacillus subtilis, Bacillus amyloliquefaciens, Bacillus licheniformis, Pseudomonas aeruginosa, Streptococcus* spp., and many others as are listed herein.

In some embodiments, the additional microbial cultures comprise microorganisms capable of accumulating nanoparticles of minerals and/or metals such as, for example, copper, cobalt, lithium, gold and/or silver, by solubilizing the metal present in ore to a soluble ionic form and converting it into nanoparticles within their cells. For example, thermophilic and/or acidophilic bacteria such as *Cupriavidus metalli-*

*durans*, which can precipitate nanoparticles of gold, can be added to the biological leaching reagent as an enhancement.

In some embodiments, the enhancing components comprise additional biosurfactants. The biosurfactants can be added as part of a microbial culture, or as a crude or purified form after being extracted from a microbial culture.

Biosurfactants are a structurally diverse group of surface-active substances produced by microorganisms. Biosurfactants are biodegradable and can be efficiently produced, according to the subject invention, using selected organisms on renewable substrates. Most biosurfactant-producing organisms produce biosurfactants in response to the presence of a hydrocarbon source (e.g. oils, sugar, glycerol, etc.) in the growing media. Other media components such as concentration of iron can also affect biosurfactant production significantly.

Microbial biosurfactants are produced by a variety of microorganisms such as bacteria, fungi, and yeasts. Exemplary biosurfactant-producing microorganisms include *Starmerella* spp. (e.g., *S. bombicola*), *Pseudomonas* spp. (e.g., *P. aeruginosa, P. putida, P. florescens, P. fragi, P. syringae*); *Flavobacterium* spp.; *Bacillus* spp. (e.g., *B. subtilis, B. amyloliquefaciens, B. pumillus, B. cereus, B. licheniformis*); *Wickerhamomyces* spp. (e.g., *W. anomalus*), *Candida* spp. (e.g., *C. albicans, C. rugosa, C. tropicalis, C. lipolytica, C. torulopsis*); *Saccharomyces* (e.g., *S. cerevisiae*); *Pseudozyma* spp. (e.g., *P. aphidis*); *Rhodococcus* spp. (e.g., *R. erythropolis*); *Arthrobacter* spp.; *Campylobacter* spp.; *Corynebacterium* spp.; *Pichia* spp. (e.g., *P. guilliermondii, P. occidentalis*); as well as others.

Biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances and increase the water bioavailability of such substances. Biosurfactants accumulate at interfaces, thus reducing interfacial tension and leading to the formation of aggregated micellar structures in solution.

The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

In certain embodiments, the biosurfactants according to the subject invention can comprise glycolipids, cellobiose lipids, lipopeptides, flavolipids, phospholipids, and polymers such as lipoproteins, lipopolysaccharide-protein complexes, and/or polysaccharide-protein-fatty acid complexes.

In some embodiments, the biosurfactants are glycolipids such as, for example, rhamnolipids (RLP), sophorolipids (SLP), trehalose lipids or mannosylerythritol lipids (MEL). In some embodiments, the biosurfactants are lipopeptides, such as, e.g., surfactin, iturin, fengycin, viscosin and/or lichenysin. In some embodiments, the biosurfactants are polymeric biosurfactants, such as, for example, emulsan, lipomanan, alasan, and/or liposan.

In one embodiment, the biological leaching reagent comprises, and/or is enhanced by the addition of, more than one biosurfactant and/or biosurfactant derivative. The biosurfactants may be mixed at any ratio as long as the composition contains the biosurfactants at concentration of 0.01 to 90%, preferably 0.05 to 50%, and more preferably 0.1 to 20%. In another embodiment, purified biosurfactants may be in combination with an accepted carrier, in that biosurfactants may be presented at concentrations of 0.0001 to 50% (v/v), preferably, 0.005 to 20% (v/v), more preferably, 0.001 to 5% (v/v).

In an exemplary embodiment, the biosurfactant is SLP. The SLP may be in a purified form or in crude form. The SLP may be added at concentrations of 0.01 to 90%, preferably 0.05 to 50%, and more preferably 0.1 to 20 wt %.

The microbe-based composition can comprise the fermentation medium containing the microorganism and/or the microbial metabolites produced by the microorganism and/or any residual nutrients. The product may be, for example, at least, by weight, 1%, 5%, 10%, 25%, 50%, 75%, or 99% growth medium. The amount of biomass in the product, by weight, may be, for example, anywhere from 0% to 100% inclusive of all percentages therebetween. For example, the biomass content of the fermentation broth may be, for example from 5 g/l to 180 g/l or more. In one embodiment, the solids content of the broth is from 10 g/l to 150 g/l.

Further components can be added to the microbe-based composition, for example, buffering agents, carriers, other microbe-based compositions produced at the same or different facility, viscosity modifiers, preservatives, nutrients for microbe growth, tracking agents, biocide, other microbes, surfactants, emulsifying agents, lubricants, solubility controlling agents, pH adjusting agents, stabilizers and ultra-violet light resistant agents.

In one embodiment, other leaching reagents can be added to the composition, or used in combination with it, for enhanced extraction of valuable minerals and/or metals. For example, acids, solvents, enzymes, proteins, peptides, sulfates and/or amino acids, produced by microbes or elsewhere, can be used, as well as other known leaching products. Preferably, any additional reagents are considered non-toxic and environmentally-friendly.

Growth of Microbes

The subject invention provides methods for cultivation of microorganisms and production of microbial metabolites and/or other by-products of microbial growth. In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The growth vessel used for growing microorganisms can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, isopropyl, propanol, butanol, pentanol, hexanol, isobutanol, and/or glycerol; fats and oils such as soybean oil, rice bran oil, canola oil, olive oil, corn oil, sesame oil, and/or linseed oil; etc. These carbon sources may be used independently or in a combination of two or more.

In one embodiment, the method comprises use of two carbon sources, one of which is a saturated oil selected from canola, vegetable, corn, coconut, olive, or any other oil suitable for use in, for example, cooking. In a specific embodiment, the saturated oil is 15% canola oil or discarded oil that has been used for cooking.

In one embodiment, the microorganisms can be grown on a solid or semi-solid substrate, such as, for example, corn, wheat, soybean, chickpeas, beans, oatmeal, pasta, rice, and/or flours or meals of any of these or other similar substances.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium chloride and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention provides methods of producing a microbial metabolite by cultivating a microbe strain of the subject invention under conditions appropriate for growth and production of the metabolite; and, optionally, purifying the metabolite. In a specific embodiment, the metabolite is a biosurfactant. The metabolite may also be, for example, ethanol, lactic acid, beta-glucan, proteins, amino acids, peptides, metabolic intermediates, polyunsaturated fatty acids, and lipids. The metabolite content produced by the method can be, for example, at least 20%, 30%, 40%, 50%, 60%, 70%, 80%, or 90%.

The biomass content of the fermentation medium may be, for example from 5 g/l to 180 g/l or more. In one embodiment, the solids content of the medium is from 10 g/l to 150 Wl.

The microbial growth by-product produced by microorganisms of interest may be retained in the microorganisms or secreted into the growth medium. In another embodiment, the method for producing microbial growth by-product may further comprise steps of concentrating and purifying the microbial growth by-product of interest. In a further embodiment, the medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a microbe-free medium or contain cells, spores, mycelia, conidia or other microbial propagules. In this manner, a quasi-continuous system is created.

Advantageously, the methods of cultivation do not require complicated equipment or high energy consumption. The microorganisms of interest can be cultivated at small or large scale on site and utilized, even being still-mixed with their media. Similarly, the microbial metabolites can also be produced at large quantities at the site of need.

Microbial Strains

The microorganisms useful according to the subject invention can be, for example, bacteria, yeast and/or fungi. Preferably, the microorganisms are capable of producing, for example, biosurfactants, enzymes, proteins, peptides, amino acids and/or solvents.

These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is any yeast or fungus. Examples of yeast and fungus species suitable for use according to the current invention, include, but are not limited to, Acaulospora, Aspergillus, Aureobasidium (e.g., A. pullulans), Blakeslea, Candida (e.g., C. albicans, C. apicola), Debaryomyces (e.g., D. hansenii), Entomophthora, Fusarium, Hanseniaspora (e.g., H. uvarum), Hansenula, Issatchenkia, Kluyveromyces, Mortierella, Mucor (e.g., M. piriformis), Penicillium, Phythium, Phycomyces, Pichia (e.g., P. anomala, P. guielliermondii, P. occidentalis, P. kudriavzevii), Pseudozyma (e.g., P. aphidis), Rhizopus, Saccharomyces (S. cerevisiae, S. boulardii sequela, S. torula), Starmerella (e.g., S. bombicola), Torulopsis, Thraustochytrium, Trichoderma (e.g., T. reesei, T. harzianum, T. virens), Ustilago (e.g., U. maydis), Wickerhamomyces (e.g., W. anomalus), Williopsis, Zygosaccharomyces (e.g., Z. bailii).

In some embodiments, the microorganisms are bacteria, including Gram-positive and Gram-negative bacteria. Bacteria suitable for use according to the present invention include, for example, Acinetobacter (e.g., A. calcoaceticus, A. venetianus); Agrobacterium (e.g., A. radiobacter), Azotobacter (A. vinelandii, A. chroococcum), Azospirillum (e.g., A. brasiliensis), Bacillus (e.g., B. amyloliquefaciens, B. firmus, B. laterosporus, B. licheniformis, B. megaterium, B. mucilaginosus, B. subtilis, B. coagulans GBI-30 (BC30)), Chlorobiaceae spp., Dyadobacter fermenters, Frankia spp., Frateuria (e.g., F. aurantia), Klebsiella spp., Microbacterium (e.g., M laevaniformans), Pantoea (e.g., P. agglomerans), Pseudomonas (e.g., P. aeruginosa, P. chlororaphis, P. chlororaphis subsp. aureofaciens (Kluyver), P. putida), Rhizobium spp., Rhodospirillum (e.g., R. rubrum), Sphingomonas (e.g., S. paucimobilis), and/or Xanthomonas spp.

In specific embodiments, the microorganism is the yeast Starmerella bombicola, which is an efficient producer of glycolipids, e.g., sophorolipids.

In some embodiments, the microorganism can be other biosurfactant- or other biochemical-producing microbes, such as, for example, Wickerhamomyces anomalus, Pseudozyma aphidis, Saccharomyces cerevisiae, Pichia guilliermondii, Bacillus subtilis, Bacillus amyloliquefaciens, Bacillus licheniformis, Pseudomonas aeruginosa, Streptococcus spp., and many others.

In some embodiments, the microorganism according to the subject invention is capable of solubilizing valuable minerals, such as, e.g., Cupriavidus matallidurans, which can accumulate nanoparticles of gold within its cells. Other examples of such microbes that are capable of reducing, oxidizing, and/or sequestering mineral components include, but are not limited to, Bacillus spp., Sulfolobus spp., Thermoanaerobacter spp., Thiobacillus spp., Penicillium spp., Aspergillus spp., Sporosarcina spp., Pseudomonas spp., Pyrobaculum spp., Deinococcus geothermalis, Marinobacter pelagius, and Delftia acidovorans Other microbial strains can be used in accordance with the subject invention, including, for example, any other strains having high concentrations of mannoprotein and/or beta-glucan in their cell walls and/or that are capable of producing biosurfactants and other metabolites useful for sequestering, solubilizing and/or recovering minerals and metals from ore.

Preparation of Microbe-Based Products

The subject invention provides microbe-based products for use in recovering valuable minerals and/or metals from ore. One microbe-based product of the subject invention is simply the fermentation medium containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microbes and/or medium (e.g., broth or solid substrate) resulting from the microbial growth can be removed from the growth vessel and transferred for immediate use.

In one embodiment, the microbe-based product is simply the growth by-products of the microorganism collected from fermentation medium in crude form, comprising, for example, about 0.001% to 99% biosurfactant in liquid broth.

In one embodiment, the microbe-based product is a yeast fermentation product comprising a yeast strain and/or growth by-products thereof. The biological leaching reagent can comprise the entire fermentation broth containing microbes, biosurfactants and other growth by-products, such as, e.g., excreted metabolites and/or cell wall components.

In one embodiment, the yeast fermentation product can be obtained via submerged cultivation of a biosurfactant-producing yeast, e.g., Starmerella bombicola. This yeast is an effective producer of glycolipid biosurfactants, such as SLP. The fermentation broth after 5 days of cultivation at 25° C. can contain the yeast cell suspension and, for example, 150 g/L or more of SLP.

Alternatively, the biosurfactants can be harvested from the broth for further processing and/or purification. In one embodiment, S. bombicola produces a layer of SLP sediment in the culture comprising about 10-15% SLP, or about 4-5 g/L. In a specific embodiment, cultivation of the yeast occurs at 25-28° C. for 1 to 10 days. Advantageously, once the SLP layer is harvested from the culture, about 1-4 g/L of SLP can still remain in the supernatant, as well as yeast cell biomass and other advantageous yeast growth by-products and cellular components.

The microorganisms in the microbe-based product may be in an active or inactive form. The microbe-based products may be used without further stabilization, preservation, and storage. Advantageously, direct usage of these microbe-based products preserves a high viability of the microorganisms (if live microbes are desired), reduces the possibility of contamination from foreign agents and undesirable microorganisms, and maintains the activity of the by-products of microbial growth.

In other embodiments, the composition (microbes, medium, growth by-products, or combinations thereof) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Upon harvesting, for example, the yeast fermentation product, from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Examples of such additives include surfactants, emulsifying agents, lubricants, buffering agents, solubility controlling agents, pH adjusting agents, preservatives, stabilizers and ultra-violet light resistant agents.

In one embodiment, the product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt as polyprotic acid such as sodium bicarbonate or carbonate, sodium sulfate, sodium phosphate, sodium biphosphate, can be included in the formulation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Methods of Extracting Valuable Minerals and/or Metals from Ore

The subject invention provides a method for extracting valuable minerals and/or metals from ore, wherein the method comprises applying a biological leaching reagent of the subject invention to the ore. The method can be used for bioleaching or for bio-stimulation of, for example, heap leaching and/or column leaching operations. In a preferred embodiment, the method is used for bioleaching of valuable minerals and/or metals from ore, for example, gold, silver, copper, cobalt, lithium, nickel and zinc.

In certain embodiments, the subject invention provides a method for extracting valuable minerals and/or metals from ore, wherein the method comprises obtaining ore from, e.g., an ore deposit, said ore comprising one or more valuable minerals and/or metals, in addition to gangue; applying a biological leaching reagent comprising one or more microorganisms and/or microbial growth by-products, to the ore; allowing the valuable minerals and/or metals to separate from the ore; and collecting the valuable minerals and/or metals.

In some embodiments, the ore particles are placed into a tank, column, vat or pool and the biological leaching reagent is applied to the ore particles by being poured into the tank, column, vat or pool.

The biological leaching reagent can enhance recovery of valuable minerals and/or metals from ore due to, for example, contact with microbial cells and/or their cell surface components, metal/mineral sequestration activity by microbial cells, and/or production of microbial metabolites such as, e.g., biosurfactants, solvents, enzymes, proteins, peptides and amino acids, that can help solubilize and/or disperse metal/mineral particles in liquid solution.

The microbes can be live (or viable), or inactive at the time of application. In certain embodiments, the microorganisms can grow in situ and produce active compounds (e.g., metabolites) onsite. Consequently, a high concentration of desirable metabolites (e.g., biosurfactants, solvents, enzymes, proteins, peptides and amino acids) and the microorganisms that produce them can be achieved easily and continuously at a treatment site (e.g., an ore mining site or a heap leaching pile).

The method can further comprise adding additional materials to enhance extraction of metals, for example, nutrients for microbial growth, additional microbial cultures, such as yeast and/or bacterial cultures and/or additional pure or crude form biosurfactants, acids, solvents, enzymes, proteins, peptides and/or amino acids.

In one embodiment, the ore has been previously mined from an ore deposit. In preferred embodiments, the mined ore is crushed, micronized, ground or pulverized into smaller ore particles prior to being contacted with the biological leaching reagent. Specifically, the ore can be crushed to a target maximum size of about 0.1 micron to about 1 inch in diameter, or about 0.5 micron to about 1 mm, or about 1 micron to about 100 microns. Methods and machinery for crushing ore are well known in the art.

In one embodiment, the ore is in the form of mine tailings, or the waste products left behind after a mineral has been separated from ore.

In a specific embodiment, the method comprises applying the biological leaching reagent in liquid form to the crushed ore particles, and mixing the particles and biological leaching reagent to form a liquid slurry.

The slurry can then be left for any amount of time sufficient to leach the valuable mineral and/or metal particles from the ore. The slurry can optionally be mixed and/or circulated continuously (e.g., mechanically or using aeration) throughout the leaching time period to ensure that maximum contact is made between the ore particles and the components of the biological leaching reagent, e.g., the yeast cell surfaces.

In one embodiment, the mineral particles are sequestered by the cells of the microorganism(s) of the biological leaching reagent. In one embodiment, the mineral particles separate from the ore and are dispersed and/or float in the liquid as solution. The liquid fraction of the slurry can be siphoned, drained, filtered, or otherwise removed. The mineral particles present in the liquid can be washed to remove residual microbial cell matter, collected, and dried, incinerated, and/or processed by any other means known in the metallurgical arts.

In some embodiments collecting or removing the separated particles is carried out using known methods, including, for example, gravity, froth flotation, electrostatic separation, magnetic separation, wet size screening, dry screening and cyclone classifying. It will be readily apparent to those skilled in the art that any other method for collecting the valuable minerals from the liquid slurry may be used.

With froth flotation, in particular, hydrophobicity differences between valuable metals/minerals and remaining ore components are increased through the use of biosurfactants and other metabolites produced by the microorganisms of the subject microbe-based compositions. The flotation process is used for the separation of a large range of sulfides, carbonates and oxides prior to further refinement.

In some embodiments, the subject methods comprise applying the biological leaching reagent in liquid form to a pile or column filled with crushed ore particles, and allowing the biological leaching reagent to percolate through the particles to a collection apparatus using gravity.

In some embodiments, the method can be used for biostimulation of heap leaching processes, wherein, after the ore has been mined and crushed or ground into small particles, the small particles are placed onto a heap leach pad to form a heap of ore particles; the biological leaching agent is poured and/or sprayed onto the heap; and the biological leaching reagent is allowed to percolate through the heap to the heap leach pad using gravity.

Examples of valuable metals and/or elements that can also be extracted using the methods of the subject invention, as well as valuable minerals that produce and/or comprise those metals and/or elements, include but are not limited to cobalt (e.g., erythrite, skytterudite, cobaltite, carrollite, linnaeite, and asbolite (asbolane)); copper (e.g., chalcopyrite, chalcocite, bornite, djurleite, malachite, azurite, chrysocolla, cuprite, tenorite, native copper and brochantite); gold (e.g., native gold, electrum, tellurides, calaverite, sylvanite and petzite); silver (e.g., sulfide argentite, sulfide acanthite, native silver, sulfosalts, pyrargyrite, proustite, cerargyrite, tetrahedrites); aluminum (e.g, bauxite, gibbsite, bohmeite, diaspore); antimony (e.g., stibnite); barium (e.g., barite, witherite); cesium (e.g., pollucite); chromium (e.g., chromite); iron (e.g., hematite, magnetite, pyrite, pyrrhotite, goethite, siderite); lead (e.g., galena, cerussite, anglesite); lithium (e.g., pegmatite, spodumene, lepidolite, petalite, amblygonite, lithium carbonate); magnesium (e.g., dolomite, magnesite, brucite, carnallite, olivine); manganese (e.g., hausmannite, pyrolusite, barunite, manganite, rhodochrosite); mercury (e.g., cinnabar); molybdenum (e.g., molybdenite); nickel (e.g., pentlandite, pyrrhotite, garnierite); phosphorus (e.g., hydroxylapatite, fluorapatite, chlorapatite); platinum group (platinum, osmium, rhodium, ruthenium, palladium) (e.g., native elements or alloys of platinum group members, sperrylite); potassium (e.g., sylvite, langbeinite); rare earth elements (cerium, dysprosium, erbium, europium, gadolinium, holmium, lanthanium, lutetium, neodymium, praseodymium, samarium, scandium, terbium, thulium, ytterbium, yttrium) (e.g., bastnasite, monazite, loparite); sodium (e.g., halite, soda ash); strontium (e.g., celestite, strontianite); sulfur (e.g., native sulfur, pyrite); tin (e.g., cassiterite); titanium (e.g., scheelite, huebnerite-ferberite); uranium (e.g., uraninite, pitchblende, coffinite, carnotite, autunite); vanadium; zinc (e.g., sphalerite, zinc sulfide, smithsonite, hemimorphite); and zirconium (e.g., zircon).

Additional elements and/or minerals, the extraction of which the subject invention is useful, include, e.g., arsenic, bertrandite, bismuthinite, borax, colemanite, kernite, ulexite, sphalerite, halite, gallium, germanium, hafnium, indium, iodine, columbite, tantalite-columbite, rubidium, quartz, diamonds, garnets (almandine, pyrope and andradite), corundum, barite, calcite, clays, feldspars (e.g., orthoclase, microcline, albite); gemstones (e.g., diamonds, rubies, sapphires, emeralds, aquamarine, kunzite); gypsum; perlite; sodium carbonate; zeolites; chabazite; clinoptilolite; mordenite; wollastonite; vermiculite; talc; pyrophyllite; graphite; kyanite; andalusite; muscovite; phlogopite; menatite; magnetite; dolomite; ilmenite; wolframite; beryllium; tellurium; bismuth; technetium; potash; rock salt; sodium chloride; sodium sulfate; nahcolite; niobium; tantalum and any combination of such substances or compounds containing such substances.

Advantageously, in certain embodiments, the methods take as little as a few hours, e.g., 3 to 12 hours, to one day to leach the minerals from the ore. The amount of time, however, depends upon, for example, how finely ground the ore particles are, the volume of ore particles being processed, and what types and/or combinations of microorganisms and other components are used in the biological leaching reagent.

Additionally, in one embodiment, the subject methods reduce the amount of refining and processing needed to recover pure or nearly pure metals from ore. For example, the subject invention can be used to separate the metals in a doré bar to reduce the amount of refining that is needed.

The method can be carried out at atmospheric pressure and lower temperatures than traditional metal smelting operations. Thus, the method does not require complicated equipment or high energy consumption, and cultivation of the biological leaching reagent used in the subject method can be performed on site, for example, at an ore mine or at a leaching site.

In one embodiment, the method can be used for removing a mineral or metal contaminant from water. Specifically, the method can be used to leach arsenic that has accumulated in water. For example, the method can comprise applying the biological leaching reagent to the contaminated water at a temperature greater than or equal to 40° C. Advantageously, the arsenic accumulation in the water can be reduced by 50 to 90% using the subject method.

In one embodiment, the method can be used to absorb radioactive metals and to reduce the radioactivity thereof. For example, by applying the biological leaching reagent to pulverized radioactive ore, the method can be used for reducing the radioactivity of uranium, plutonium, radon, and other radioactive metals present in the ore.

The subject methods can be carried out at atmospheric pressure and lower temperatures than traditional metal smelting operations. Thus, the method does not require complicated equipment or high energy consumption, and cultivation of the biological leaching reagent used in the subject method can be performed on site, for example, at a mine or at a leaching site.

Advantageously, the present invention can be used without releasing large quantities of inorganic and toxic compounds into the environment. Additionally, the compositions and methods utilize components that are biodegradable and toxicologically safe, and can be used to reduce the amount of toxic waste produced during mining and leaching processes.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a mine). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a mine), for example, within 300 miles, 200 miles, or even within 100 miles. Advantageously, this allows for the compositions to be tailored for use at a specified location. The formula and potency of microbe-based compositions can be customized for specific local conditions at the time of application, such as, for example, which ore type is being treated; what type of mineral is being extracted; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve leaching processes.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Examples

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Fermentation of *Starmerella bombicola* for Biosurfactant Production in a 2000 L Gallon Reactor A large-scale, fully enclosed reactor is used. The reactor has a working volume of 1500 L when growing *S. bombicola* for SLP production.

In some embodiments, the nutrients for SLP production are glucose, urea, yeast extract, canola oil, magnesium sulfate, and potassium phosphate.

The reactor is inoculated with 10 liters of liquid culture grown separately in inoculum reactors. The duration of the cultivation cycle for SLP production is up to 120 hours, at 25° C. and pH 3.5, with sampling performed once a day.

The final concentration of SLP is 70 gallons, with SLP concentration of 300-400 g/L. The entire broth can be harvested, containing SLP and yeast cells, and used directly.

Alternatively, the SLP can be extracted from the final product and used with or without purification and/or concentration. The remaining supernatant with cell biomass can also be used, comprising 1-4 g/L of residual SLP.

Example 2—Production of Lipopeptides by *Bacillus* Spp.

Fermentation of *Bacillus* bacteria can be performed in a nutrient medium containing (g/L), for example:

| | |
|---|---|
| Glucose | 18 |
| Powder molasses | 2 |
| Sucrose | 1 |
| $KH_2PO_4$ | 0.5 |
| $Na_2HPO_4 \cdot 7H_2O$ | 2.1 |
| KCl | 0.1 |
| $MgSO_4$ | 0.5 |
| $CaCl_2$ | 0.05 |
| Urea | 2.5 |
| $NH_4Cl$ | 1.24 |
| Yeast extract | 2 |
| Corn peptone | 0.5 |
| TekNova trace element (mL) | 1 |
| pH 6.8 | |

Temperature of cultivation is about 40° C., pH stabilization is from 6.8-7.0, and DO stabilization is at 30% (concentration of oxygen in the air is taken as 100%). Duration of cultivation is 24-32 hours. The final concentration of bacterial culture is no less than $1 \times 10^9$ CFU/ml. The concentration of lipopeptides is 5-10 g/L.

REFERENCES

Blog, Gold/Silver/Rare Coins. *Precious Metals in Order of Value*. Biltmore Loan and Jewelry; [updated 21 Feb. 2016; accessed 20 Nov. 2018]. https://www.biltmore-loanandjewelry.com/blog/precious-metals-in-order-of-value/. (Biltmore Loan and Jewelry 2016).

We claim:

1. A method for extracting minerals and/or metals from ore, the method comprising:
   obtaining ore comprising one or more minerals and/or metals selected from the group consisting of gold, silver, copper, cobalt, lithium, zinc and nickel, and gangue;
   crushing, grinding, micronizing or pulverizing the ore into smaller ore particles; applying a biological leaching reagent comprising a *Starmerella bombicola* yeast and/or a growth by-product thereof to the ore particles, wherein the growth by-product is a biosurfactant;
   mixing the biological leaching reagent with the ore particles to form a slurry;
   allowing the minerals and/or metals to separate from the ore; and
   collecting the minerals and/or metals from the slurry.
2. The method of claim 1, wherein the mixing occurs continuously.
3. The method of claim 1, wherein the separated minerals and/or metals are dispersed and/or float in the slurry as solution.
4. The method of claim 1, wherein the separated minerals and/or metals are sequestered by the yeast and/or growth by-product thereof of the biological leaching reagent.
5. The method of claim 1, wherein the minerals and/or metals are collected from the slurry via gravity, froth flotation, electrostatic separation, magnetic separation, wet size screening, dry screening or cyclone classifying.
6. The method of claim 1, wherein the ore is in the form of mine tailings.
7. The method of claim 1, wherein contacting the ore with the biological leaching reagent comprises placing the ore particles into a tank, column, vat or pool and pouring the biological leaching reagent into the tank, column, vat or pool.
8. The method of claim 1, wherein the biological leaching reagent further comprises glycine.

* * * * *